United States Patent [19]

Kurata

[11] 4,188,360

[45] Feb. 12, 1980

[54] ARTIFICIAL LUNG WITH A BUILT-IN HEAT EXCHANGER

[75] Inventor: Motoji Kurata, Hiroshima, Japan

[73] Assignee: Japan Medical Supply Co., Ltd., Hiroshima, Japan

[21] Appl. No.: 940,737

[22] Filed: Sep. 8, 1978

[51] Int. Cl.² .............................................. A61M 1/03
[52] U.S. Cl. ............................... 422/46; 128/DIG. 3; 261/DIG. 28; 422/47
[58] Field of Search .................................. 422/46, 47; 23/258.5 BH, 258.5 MH; 128/DIG. 3; 261/DIG. 28

[56] References Cited

U.S. PATENT DOCUMENTS

| | | |
|---|---|---|
| 3,768,977 | 10/1973 | Brumfield et al. ...................... 422/46 |
| 3,769,162 | 10/1973 | Brumfield ........................... 422/46 X |
| 3,807,958 | 4/1974 | Brumfield et al. ...................... 422/46 |
| 4,065,264 | 12/1977 | Lewin .................................... 422/46 |

FOREIGN PATENT DOCUMENTS 2332446  1/1975  Fed. Rep. of Germany ............. 422/46

Primary Examiner—Barry S. Richman
Attorney, Agent, or Firm—Armstrong, Nikaido, Marmelstein & Kubovcik

[57] ABSTRACT

An artificial lung provided with a built-in heat exchanger comprising an outer cylindrical member, an inner cylindrical member and an intermediate cylindrical member disposed between said outer and inner cylindrical members.

A plurality of tubes are disposed within said inner cylindrical member through which a heat exchange medium is adapted to pass. The supply of oxygen to the blood is carried out within the inner cylindrical member while heat exchange is performed between the blood and the heat exchange medium.

4 Claims, 2 Drawing Figures

4,188,360

ARTIFICIAL LUNG WITH A BUILT-IN HEAT EXCHANGER

BACKGROUND OF THE INVENTION

This invention relates to an artificial lung having a built-in heat exchanger. In general in case of conducting an operation to the heart of a patient, it is required on substitute temporarily a blood circulation system outside his body for the function of his heart and lung. The abovementioned blood circulation system which has conventionally been employed comprises an artificial lung for supplying oxygen to the blood and a heat exchanger for controlling the temperature of the blood. However, the conventional artificial lung device is disadvantageous in that because the main body and heat exchanger are formed separately much labour and time are required to sterilize them and connect the component parts by means of conduits to thereby form a blood circulation system outside the patient's body. Further, because even the conduits connecting the component parts are required to be filled with the blood, a great deal of blood is required to allow the blood circulation system outside the patient's body to function satisfactorily.

SUMMARY OF THE INVENTION

It is therefore an object of the present invention to provide an artificial lung having a built-in heat exchanger.

Another object of the present invention is to provide an artificial lung wherein the amount of supply of the blood needed to operate it is considerably reduced.

A further object of the present invention is to provide an artificial lung wherein the efficiency of supplying oxygen to the blood is significantly improved.

In accordance with an aspect of the present invention, there is provided an artificial lung provided with a built-in heat exchanger comprising an outer cylindrical member, an inner cylindrical member and an intermediate cylindrical member disposed therebetween. A lower portion of said inner cylindrical member is extended beyond the bottom wall of said outer cylindrical member and has an oxygen dispenser plate, an intermediate plate and a bottom plate formed therein defining an oxygen inlet chamber and an heat-exchange medium chamber therebetween, respectively.

The heat exchange chamber has a partition wall formed therein so as to divide the same into a heat exchange medium inlet chamber and a heat exchange medium outlet chamber.

The lower portion of said inner cylindrical member also has an inlet for blood formed therein, an inlet for oxygen formed therein which is connected to said oxygen inlet chamber, and an inlet and an outlet for a heat exchange medium formed therein and which are connected to said heat exchange medium inlet chamber and said heat-exchange medium outlet chamber, respectively. The oxygen dispenser plate has a plurality of perforations formed therein so as to allow oxygen to pass therethrough.

A return chamber is provided in the upper wall of said outer cylindrical member. A plurality of tubes are disposed within said inner cylindrical member, the upper ends thereof being connected to said return chamber and the lower ends thereof being connected to either said heat-exchange medium inlet chamber or said heat exchange outlet chamber.

A foam or bubble extinguishing chamber is defined between said inner and intermediate chambers in which a defoaming agent is charged.

Oxygen is supplied to blood within said inner chamber, while heat exchange is carried out between the blood and the heat exchange medium passing through the plurality of tubes.

The above and others objects, features and advantages of the present invention will be readily apparent from the following description taken in conjunction with the accompanying drawings.

DETAILED DESCRIPTION OF THE INVENTION

Figure 1:
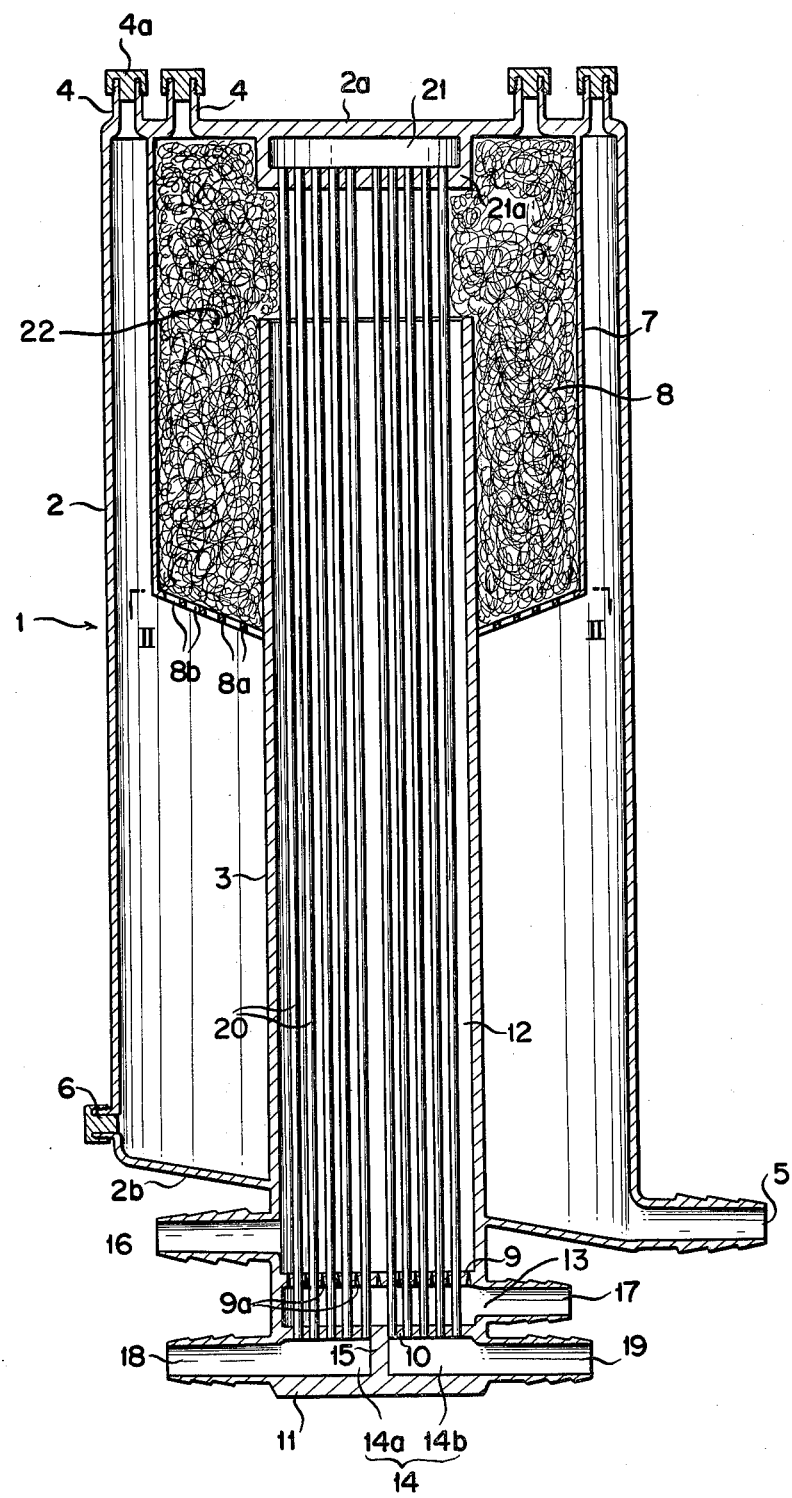
FIG. 1 is a longitudinal cross-sectional view of an artificial lung according to the present invention.
Figure 2:
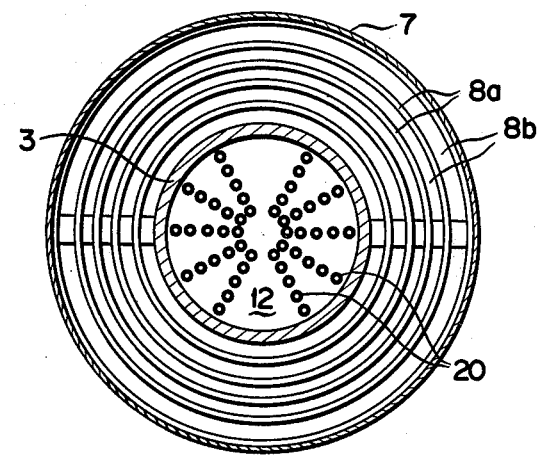
FIG. 2 is a cross-sectional view taken along the line II—II in FIG. 1.

The present invention will now be described in detail below by way of embodiment with reference to the accompanying drawings. In the drawings, reference numeral 1 denotes an artificial lung's body which comprises an outer cylindrical member 2 made by transparent glass or plastic material and an inner cylindrical member 3 having a smaller diameter than that of the outer member 2 and located concentrically in the central part thereof. The above-mentioned outer cylindrical member 2 has an upper face closed by an upper plate 2a having a plurality of air venting louver 4 and a lower face closed by a bottom plate 2b inclining towards an outlet 5 for the arterial blood. Reference numeral 6 indicates a louver or vent for sampling the arterial blood.

Further, the upper end of the inner cylindrical member 3 is located off from the upper plate 2a of the outer cylindrical member 2 and is arranged to communicate with a defoaming chamber 8 formed by a cylindrical partition wall or an intermediate cylindrical member 7 in the upper part of the outer cylindrical member 2. The lower end of the inner cylindrical member 3 extends through the bottom plate 2b of the outer cylindrical member 2 and projects below the latter. The lower end of the inner cylindrical member 2 is divided by an oxygen dispenser plate 9 having a plurality of small perforations 9a, a tube or intermediate plate 10 and a bottom plate 11 into a heat exchange chamber 12, an oxygen gas inlet chamber 13 and a heat exchange medium inlet and outlet chamber 14. The heat exchange medium inlet and outlet chamber 14 is divided by a partition wall 15 formed between the bottom plate 11 and the tube plate 10 into a heat exchange medium inlet chamber 14a and a heat exchange medium outlet chamber 14b. The chambers 12, 13, 14a and 14b have a venous blood inlet 16, an oxygen gas inlet port 17, an heat exchange medium inlet port 18 and an heat exchange medium outlet port 19 connected thereto, respectively.

Fixedly secured to the above-mentioned tube plate 10 are the lower ends of the plurality of tubings 20 accommodated within the inner cylindrical member 3 and passing through the oxygen dispenser plate 9. On the other hand, the upper ends of the tubings 20 are fixedly secured to a tube plate 21a in the bottom part of a return chamber 21 formed below the upper plate 2a of the outer cylindrical member 2. The defoaming chamber 8 having the return chamber 21 located therein is filled with a net-shaped defoaming agent 22 which consists of long filaments of a plastic material, the surfaces of which are treated with a medically non-poisonous and chemically stable surface active agent. The defoaming chamber 8 has an inverted cone shaped bottom plate 8a having a plurality of blood dripping spacings 8b formed therein.

The air-venting louvers 4 each have a sterilized filter mounted therein so that even when the cap 4a is removed no entry of miscellaneous germs is allowed.

Thus, in operation, the blood from the heart of the patient to be subjected to an operation flows through the venous blood inlet port 16 into the heat exchange chamber 12 and is kept at a proper temperature by heat exchange effect provided by a heat exchange medium such as hot or cooled water which flows from the heat exchange medium inlet port 18 and through the inside of the tubings 20. At the same time, the oxygen fed through the oxygen gas inlet port 17 into the oxygen gas inlet chamber 13 is injected through the small holes 9a of the oxygen dispenser plate 9 into the heat exchange chamber 12 so that it is moved upwards in the form of foams in the blood within the heat exchange chamber 12 and at that time a part of the oxygen is merged into the blood thereby supplying oxygen into the blood. Since the blood within the heat exchange chamber 12 is kept at a proper temperature by the heat exchange effect of the medium passing through the inside of the tubings 20, activation of the blood can be increased thereby improving the efficiency of supplying oxygen to the blood.

The blood which has moved upwards within the heat exchange chamber 12 overflows the inner cylindrical member 3 and flows into the defoaming chamber 8 so that the air bubbles in the blood can be eliminated by the defoaming agent 22 within the chamber 8. Then, the blood will drop through the blood dropping spacings 8b formed in the bottom of the defoaming chamber 8 on the bottom of the outer cylindrical member 2 and will be returned through the arterial blood outlet port 5 into the blood tube of the patient. Further, since a part of the oxygen which has not been merged into the blood will accumulate on the upper part of the defoaming chamber 8 or the outer cylindrical member 2, it is only necessary to open the caps 4a of the air-venting louvers 4 thereby expelling the air bubbles and at that time there is no risk of miscellaneous germs entering therein due to the action of the sterilized filters.

The heat exchange medium which has flowed through the heat exchange medium inlet port 18 and the chamber 14a flows through the tubings 20 into the return chamber 21, and then flows down through the tubings 20 and the chamber 14b and is discharged through the outlet port 19. Further, a sample of the blood supplied with oxygen can be taken at any time from an arterial blood sampling louver 6. The sampling louver 6 is of a female form so that it can be easily connected with any other fitting.

As mentioned in detail hereinabove, according to the present invention, since the artificial lung body includes a built-in heat exchanger, the manpower required for connecting, locating and sterilizing the component parts can be eliminated as compared with the conventional one in which an artificial lung is connected with a separate heat exchanger by means of conduits. Therefore, a blood circulation system outside the patient's body can be prepared and operated in a short time. Further, there is no need of provision of conduits for connecting the component parts so that the amount of the blood to be charged into the artificial lung system can be reduced. Moreover, concurrently with the heat exchange oxygen can be supplied into the blood to be circulated so that the activation of the blood can be increased remarkably thereby increasing the efficiency of supplying oxygen into the blood and enabling the size of the device itself to be made smaller.

While this invention is susceptible of embodiment in many different forms, there is shown in the drawings and described herein in detail a specific embodiment of the invention, with the understanding that the present disclosure is to be considered as an exemplification of the principles of the invention and is not intended to limit the invention to the embodiment illustrated.

What is claimed is:

1. An artificial lung provided with a built-in heat exchanger comprising an outer cylindrical member having top and bottom walls and an outlet for blood formed in a lower portion thereof;

an inner cylindrical member disposed within said outer cylindrical member with a lower portion thereof extending through the bottom wall of said outer cylindrical member, the lower portion of said cylindrical member having an oxygen dispenser plate, an intermediate plate and a bottom plate formed therein defining an oxygen inlet chamber and a heat-exchange medium chamber therebetween, respectively, the heat-exchange medium chamber having a partition wall formed therein to divide the same into a heat exchange medium inlet chamber and a heat exchange medium outlet chamber, the lower portion of said inner cylindrical member also having an inlet for blood formed therein, an inlet for oxygen connected to said oxygen inlet chamber, and an inlet and outlet for heat exchange medium connected to said heat exchange medium inlet chamber and said heat exchange medium outlet chamber, resectively, an intermediate cylindrical member disposed between said outer and inner cylindrical members, said intermediate cylindrical member including a bottom wall having spacings formed therein defining a defoaming chamber between said inner and intermediate cylindrical members; and a plurality of tubes disposed within said inner cylindrical member through which heat exchange medium is passed, said plurality of tubes passing through said oxygen inlet chamber and said heat exchange medium chamber, wherein oxygen supplied to said inlet chamber through said oxygen inlet and blood supplied to said inner chamber through said blood inlet are in contact with said heat exchange medium carrying tubes prior to being brought into contact with one another.

2. The artificial lung as defined in claim 1 wherein a return chamber is provided in the upper wall of said outer cylindrical member and wherein upper ends of said plurality of tubes are connected to said return chamber while lower ends thereof are connected to either said heat exchange medium inlet chamber or to said heat exchange medium outlet chamber.

3. The artificial lung as defined in claim 1 or 2 wherein a defoaming agent is charged in said defoaming chamber and wherein the upper end of said inner cylindrical member is communicated with said defoaming chamber.

4. The artificial lung as defined in claim 1 or 2 wherein said oxygen dispenser plate has a plurality of perforations formed therein to allow oxygen to pass therethrough.

* * * * *